United States Patent
Akridge et al.

(10) Patent No.: US 10,441,764 B2
(45) Date of Patent: Oct. 15, 2019

(54) SONIC APPLICATOR FOR SKIN FORMULATIONS

(76) Inventors: Robert E. Akridge, Seattle, WA (US); David Giuliani, Mercer Island, WA (US); Christopher J. McEvoy, Seattle, WA (US); Kenneth A. Pilcher, Seattle, WA (US); Richard A. Reishus, Renton, WA (US)

( * ) Notice: Subject to any disclaimer, the term of this patent is extended or adjusted under 35 U.S.C. 154(b) by 1278 days.

(21) Appl. No.: 12/135,887

(22) Filed: Jun. 9, 2008

(65) Prior Publication Data
US 2009/0306577 A1 Dec. 10, 2009

(51) Int. Cl.
*A61M 37/00* (2006.01)
*A61M 35/00* (2006.01)

(52) U.S. Cl.
CPC .......... *A61M 37/00* (2013.01); *A61M 35/003* (2013.01); *A61M 37/0092* (2013.01); *A61M 2037/0007* (2013.01)

(58) Field of Classification Search
CPC .......... A61M 2037/0007; A61M 37/00; A61M 37/0092; A61M 2205/058; A61M 35/003; A61H 2201/105; A61H 23/0245; A61H 23/04; A61H 15/02; A61D 2200/207
USPC ..... 604/20, 232, 519, 17, 64, 110, 890.1, 22
See application file for complete search history.

(56) References Cited

U.S. PATENT DOCUMENTS

| | | | | |
|---|---|---|---|---|
| 3,526,219 A | * | 9/1970 | Balamuth | A61B 17/320068 175/56 |
| 4,088,128 A | * | 5/1978 | Mabuchi | A61H 23/0254 601/101 |
| 4,549,535 A | * | 10/1985 | Wing | A61H 23/0218 310/35 |
| 4,566,442 A | * | 1/1986 | Mabuchi | A61H 23/0254 601/101 |
| 4,827,914 A | * | 5/1989 | Kamazawa | A61H 23/0254 601/101 |
| 5,279,284 A | * | 1/1994 | Fenn | A61H 23/0218 601/108 |
| 5,391,144 A | * | 2/1995 | Sakurai | A61B 17/22012 601/3 |
| 6,305,863 B1 | * | 10/2001 | Gueret | A45D 34/045 401/126 |
| 6,488,661 B1 | * | 12/2002 | Spohn | A61M 5/488 604/151 |
| 2002/0195884 A1 | * | 12/2002 | Ichii | A61C 17/34 310/15 |
| 2003/0009153 A1 | * | 1/2003 | Brisken et al. | 604/890.1 |

(Continued)

*Primary Examiner* — Emily L Schmidt
(74) *Attorney, Agent, or Firm* — Jensen & Puntigam, P.S.; Clark A. Puntigam

(57) ABSTRACT

The applicator includes a housing and a motor contained therewithin which includes an output member, such as a shaft, which in operation moves in a reciprocating manner. A contact member is mounted for operation and moves in response to the action of the output shaft, such that the contact element in operation repeatedly contacts a selected skin area, moving toward and away from the skin area, substantially perpendicularly thereto. The contact member moves at a frequency within the range of 50 Hz to 200 Hz and with an amplitude of 0.010 to 0.075 inches. The repeated tapping action of the contact member against the skin increases the absorption of a skin formulation into the skin area being contacted.

24 Claims, 11 Drawing Sheets

(56) References Cited

U.S. PATENT DOCUMENTS

| | | | |
|---|---|---|---|
| 2004/0015139 A1* | 1/2004 | La Bianco | A61B 17/54 604/289 |
| 2005/0142093 A1* | 6/2005 | Skover | A61B 17/54 424/70.14 |
| 2005/0277950 A1* | 12/2005 | Pilcher | A61B 17/54 606/131 |
| 2005/0278877 A1* | 12/2005 | Akridge et al. | 15/28 |
| 2005/0280319 A1* | 12/2005 | Pilcher et al. | 310/36 |
| 2006/0025710 A1* | 2/2006 | Schulz | A61H 23/0218 601/108 |
| 2006/0058714 A1* | 3/2006 | Rhoades | A45D 24/007 601/73 |
| 2013/0137951 A1* | 5/2013 | Chuang et al. | 600/364 |

* cited by examiner

 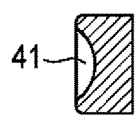 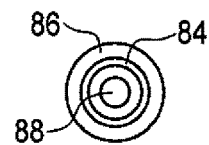 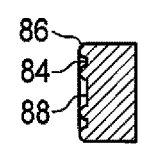
FIG. 6A  FIG. 6B  FIG. 8A  FIG. 8B
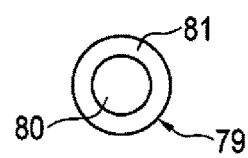 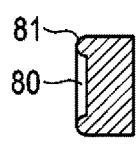  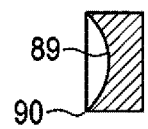
FIG. 7A  FIG. 7B  FIG. 9A  FIG. 9B
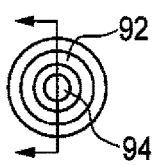 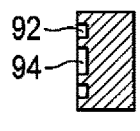 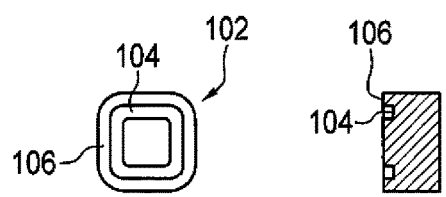 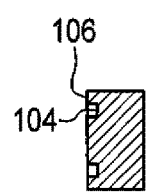
FIG. 10A  FIG. 10B  FIG. 12A  FIG. 12B
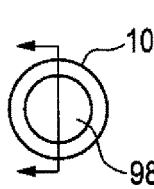 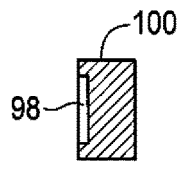 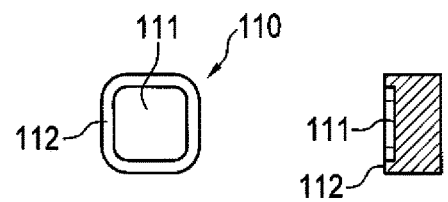 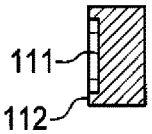
FIG. 11A  FIG. 11B  FIG. 13A  FIG. 13B
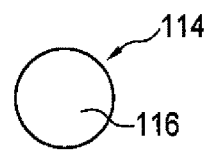 
FIG. 14A  FIG. 14B

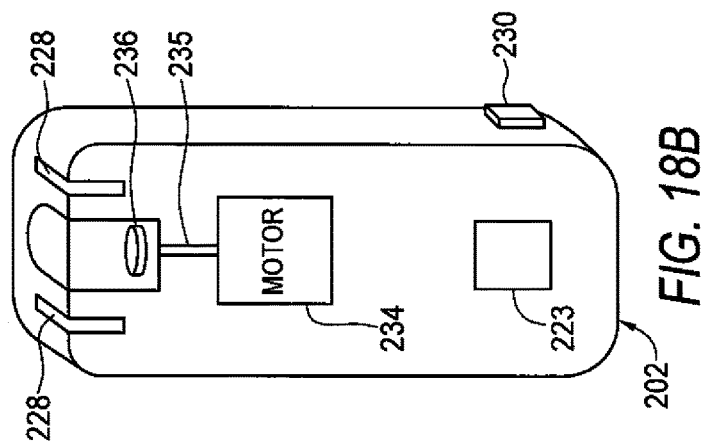
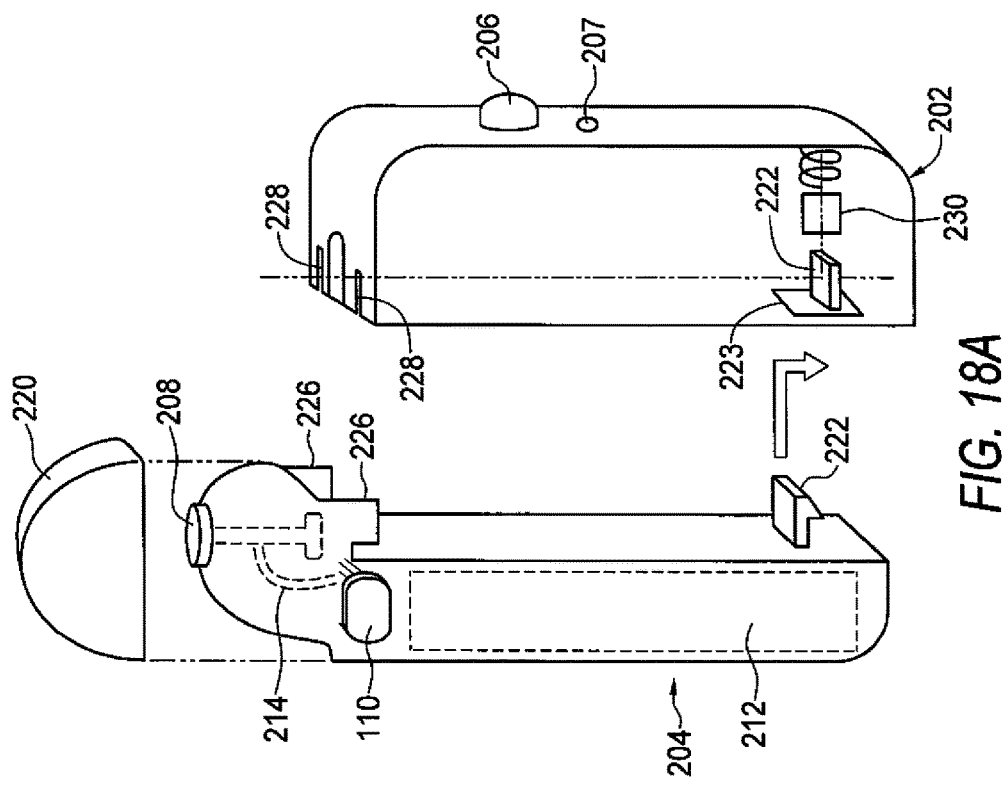
FIG. 18B
FIG. 18A

SONIC APPLICATOR FOR SKIN FORMULATIONS

TECHNICAL FIELD

This invention relates generally to the application of skin treatment formulations to selected skin areas of the human body and more particularly concerns, an apparatus to accomplish the application of skin formulations to the body, particularly the facial area.

BACKGROUND OF THE INVENTION

In recent years, there have been significant advances in skincare regimens, consisting typically of three components: (1) cleansing, (2) treating and (3) protection, of the skin. However, skincare is still often a laborious task, requiring consistent effort, with unsatisfactory results being not unusual. Consumers often feel dissatisfied because of the relatively low level absorption into the skin of often quite expensive cosmetic formulations and the time required of use of formulations before they see definite results. Insufficient absorption into the skin of these formulations, results in sub-optimal performance of the formulations. Absorption is thus believed to be important to the overall effectiveness of the formulation.

Historically, there are a number of methods for applying various formulations to the skin. In an approach using chemicals, the formulations themselves contain substances which are thought to speed and/or increase absorption. This includes some acidic formulations, imidazole, propylene glycol and isopropyl myristate as well as the use of liposomes in the formulations, all of which, however, have undesirable side effects or toxicity.

Manual methods are also often used, with cosmetic skincare associates who are trained to apply the formulations by tapping the area of the skin to which the formulation has been applied with a finger, typically the ring finger, as opposed to rubbing the solution into the skin.

Another method of application concerns the use of non-motorized applicators, which may include an extending wand member with an assembly on one end for applying the formulation to the skin. One such assembly consists of a roller or plastic balls which comprise materials which absorb the formulation. The applicator is then simply rolled across the skin area being treated.

Motorized devices are also used which include low-frequency sound or galvanic; current arrangements which allegedly enhance the penetration of the formulation into the skin. These devices, however, typically have the disadvantage of being able to treat only a very small area at a time. Other devices use ultrasonic therapy or ion therapy in a handheld device.

Still other applicators include passive elements, such as small pieces of cloth impregnated with the formulation, which are then applied directly to the skin and kept in place for an extended period of time, e.g. overnight.

All of the above articles or methods however, have one or more significant disadvantages, including inconvenience, cost, time required to experience results and/or lack of proven results.

Hence, it is desirable to have an applicator system or article which can reliably increase the penetration of formulations into the skin of a user.

SUMMARY OF THE INVENTION

Accordingly, a formulation applicator for skin areas of the human body is disclosed herein, comprising: a housing; a motor contained within the housing having a output member portion which moves in a reciprocating manner; and a contact member mounted on the output member, which in operation repeatedly impacts the skin area, the contact element moving in a frequency of 50 Hz to 200 Hz and an amplitude in the range of 0.010-0.075 inches, toward and away from the skin area, acting to increase the absorption of formulations into the skin area as the contact element impacts the skin area to which the formulation is being applied.

In addition, a formulation applicator for skin areas of the human body is disclosed herein comprising: a housing; a motor assembly having an output drive member which moves in a reciprocating manner; a cartridge assembly connectable to and removable from the motor assembly, containing a formulation reservoir, a contact assembly which includes a contact member and a fluid-directing assembly which moves fluid, in response to operation of an actuating member, from the reservoir to the contact, member, wherein the contact assembly is moved by the motor assembly, the contact member impacting the skin area, moving at a frequency of 50 Hz to 200 Hz and with an amplitude in the range of 0.01-0.075 inches, toward and away from the skin area, acting to increase the absorption of formulation into the skin area.

Further a method of applying: formulation to skin areas of a human body is disclosed herein comprising the step of: tapping a skin formulation into a skin area with a mechanical applicator having a contact element with a solid end face at a frequency in the range of 50 Hz to 200 Hz and an amplitude in the range of 0.01-0.075 inches, wherein the tapping is toward and away from the skin area, substantially perpendicular thereto, the tapping acting to increase the absorption of formulation into the skin area.

Still further, a motor for application of a skin formulation to a skin area is disclosed herein, comprising: a housing; an anchor member fixedly mounted to the housing; an armature having a back iron member upon which is mounted a permanent magnet assembly; two spaced spring members which connect the anchor member and the armature; a stator assembly positioned between the anchor member and the armature, the stator assembly including a coil, which when energized by an alternating current, produces a back-and-forth movement of the armature; and an applicator assembly connected to one end of the armature, with a skin contact member at a free end thereof, such that in operation, the applicator assembly and the contact member move back and forth toward and away from a skin area of the user, contacting the skin in such a manner as to increase the absorption of formulation into the skin.

BRIEF DESCRIPTION OF THE DRAWINGS

FIGS. 6(A,B)-14(A,B) are top views and cross-sectional views, respectively, of a plurality of skin contact members.

FIG. 18A is a partially exploded view of the embodiment of FIG. 17.

FIG. 18B is another view of a portion of FIG. 18A.

BEST MODE FOR CARRYING OUT THE INVENTION

Figure 1:
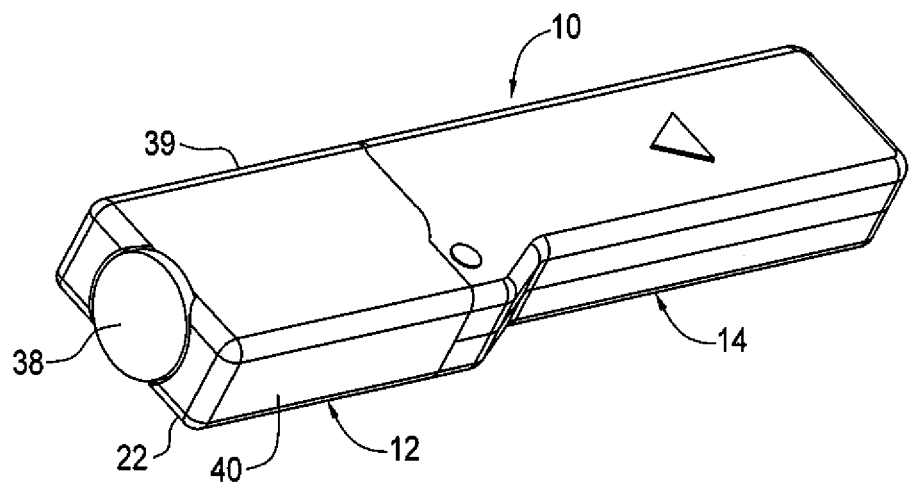
FIG. 1 is a perspective view of a fully assembled skin formulation applicator disclosed herein.
Figure 2:
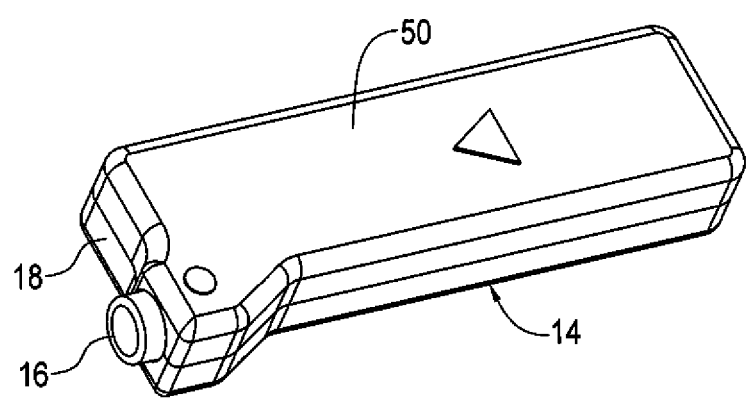
FIG. 2, is a perspective view of an applicator assembly portion of the article of FIG. 1.
Figure 3:
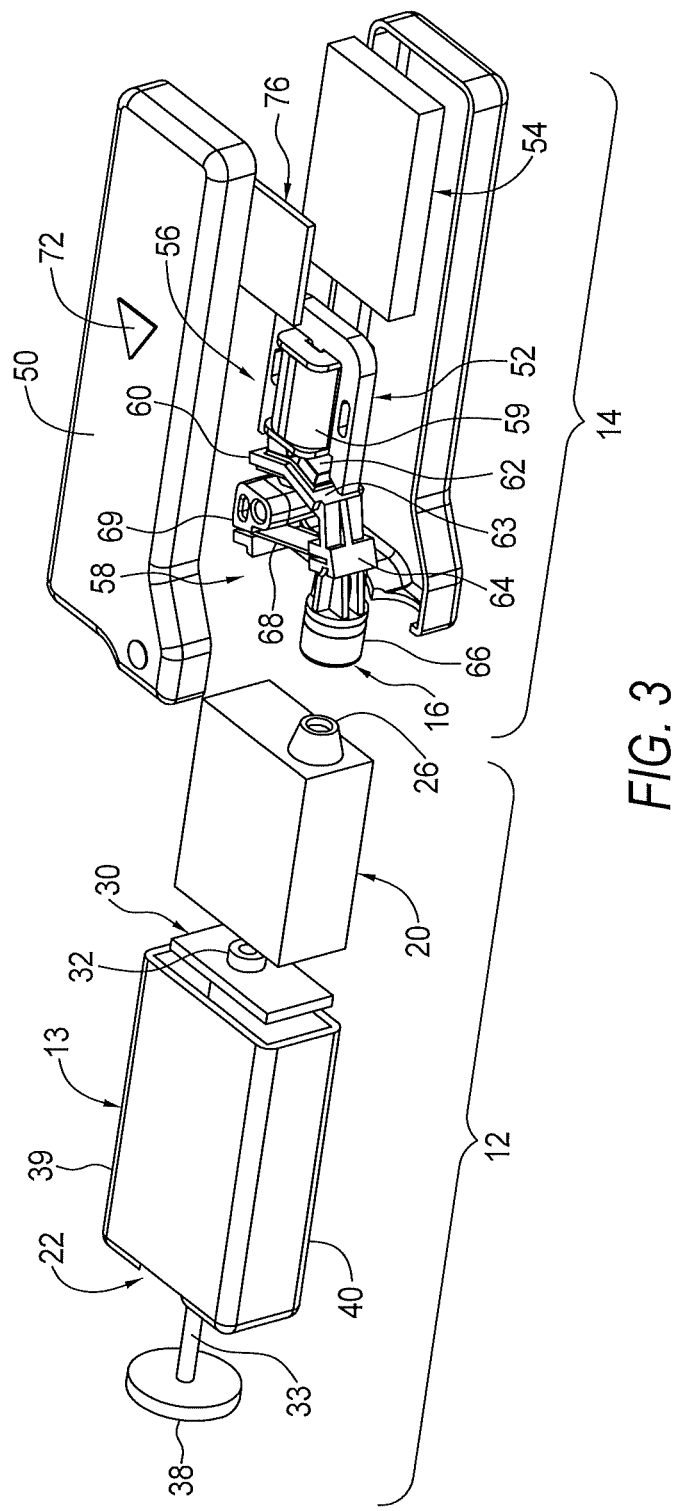
FIG. 3 is an exploded view of the article of FIG. 1.
Figure 4:
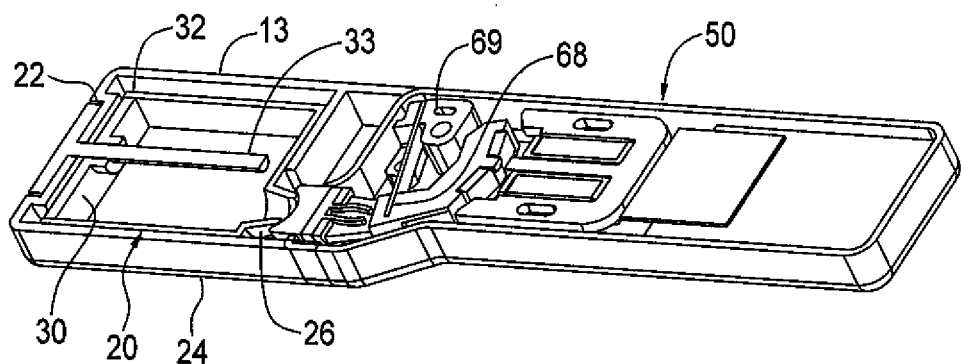
FIG. 4 is a longitudinal cross-sectional view of the article of FIG. 1.
Figure 5:
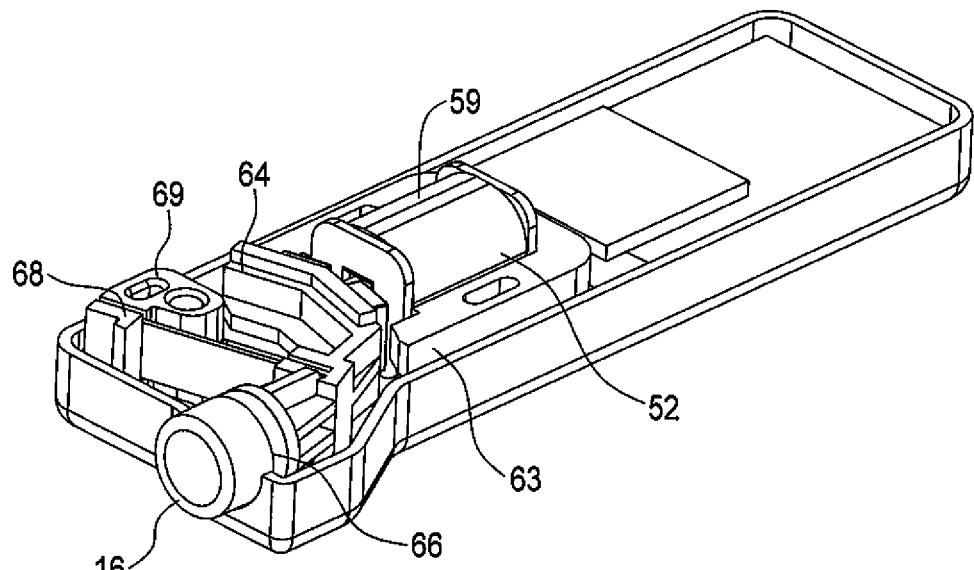
FIG. 5 is another longitudinal cross-sectional view of the article of FIG. 1.

FIGS. 1-5 show a formulation applicator apparatus 10 disclosed herein. Apparatus 10 includes a reservoir assembly portion 12 and an applicator assembly portion 14 which includes a contact member 16 at a forward end 18 thereof. Reservoir assembly portion 12 in the embodiment shown is rectangular, approximately 2.2 inches long by approximately 1.38 inches wide, and approximately 0.7 inches high. The length of the complete apparatus 10 is approximately 5.96 inches. The reservoir assembly includes a housing 13, within which is positioned a formulation reservoir 20. At the rear end 24 of reservoir 20 is a funnel-like extension 26 which is configured and positioned to fit into contact member 16 when the reservoir assembly 12 is mated with the applicator assembly 14. Alternatively, extension 26 is configured so as to be positioned away from contact member 16 when the reservoir assembly 12 is mated with the applicator assembly 14. When the reservoir assembly 12 is detached from the applicator assembly 14 by the user, the user can position the extension 26 over contact member 16 and apply the formulation directly to the contact member by use of the dispensing mechanism in the reservoir assembly, as explained below.

Positioned within reservoir 20 is a back plate 30 which has approximately the same cross-sectional dimension as the interior of formulation reservoir 20. Back plate 30 has a threaded opening 32 into which is threaded an elongated rod 33. A flat knob 38 is attached to the forward end of the elongated rod. Knob 38 is positioned at forward end 22 of the reservoir assembly 12. Knob 38 is a flat disc, typically with a knurled edge, configured so that it can be conveniently rotated by the user, and extends slightly outside of the long edges 39 and 40 of the forward end of the reservoir assembly. All of the parts of the reservoir assembly are typically made from a strong plastic material, although parts of the reservoir assembly, such as the housing, could be made from metal as well.

In operation, as the user rotates knob 38, back plate 30 moves within reservoir 20 toward the rear end thereof, forcing the formulation in the reservoir through funnel extension 26 into contact member 16 of the applicator assembly 14. Rear end 24 of reservoir assembly 12 is configured to mate snugly with the forward end 18 of the applicator assembly in a frictional fit, while still allowing the reservoir assembly to be conveniently removed from the applicator assembly when the applicator is to be used.

The applicator assembly 14 includes a housing 50. Housing 50 is approximately 1.13 inches wide over most of its length except in the vicinity of a forward end 18 thereof, where the width increases to approximately 1.38 inches to match the width of the reservoir assembly. The height of the applicator assembly is also approximately 0.67 inches. The applicator assembly is configured to be easily held in the hand of a user. Contact member 16 which extends outwardly a short distance from the forward end of the applicator assembly, is replaceable by the user. Alternatively; the contact member can be permanently attached to the applicator assembly. Contact member 16 may take various configurations, as will be discussed in more detail below. One particular embodiment (FIGS. 6A, 6B) is generally circular in outline with a diameter of approximately 0.406 inches. The height of that contact member is approximately 0.231 inches and has a dish or cup-shaped upper end surface 41, bordered by a narrow rounded lip edge 42 which allows the contact member to conveniently hold a single dose of skin formulation, although the configuration can be such as to hold other volumes of formulations, greater or less than a single dose. In the embodiment shown, contact member 16 is made from a silicone material or equivalent, including silicone gel, with a Durometer value between 00-30 and Shore A-5

In use of the applicator, the contact member, loaded with formulation, is held lightly against the skin. Action of a motor 52 positioned within housing 50 moves the contact member away from and then against, the skin of the user. In the embodiment shown, motor 52 is powered by a lithium ion rechargeable battery 54. Many alternatives are possible to the lithium ion battery, such as nickel metal hydride (NiMH) batteries and alkaline primary cells, which are field replaceable. A conventional wall power recharger can be used for recharging of the batteries. The battery or batteries can also be charged inductively using a wall powered oscillator energizing a primary coil, which in turn induces current to flow in a secondary coil in the applicator assembly.

Motor 52 includes a stator assembly 56 and an armature assembly 58. The stator assembly includes an electromagnet 59. Armature assembly 58 includes a backiron member 60 positioned in the vicinity of one end of the electromagnet and has two permanent magnets 62 mounted thereon. Extending from one end 63 of the backiron 60 is an armature arm 64 which connects to a mounting element 66 for the contact member 16. As indicated above, contact member 16 can be removably mounted to mounting element 66 so that it can be replaced from time to time if necessary.

A beam spring 68 extends between armature arm 64 and an anchor member 69 which is mounted to a housing 50 for the device. The motor 52, in general, is similar to existing motor designs. Examples are shown in U.S. Patent Publication No. 20080106156 and U.S. Pat. No. 7,157,816 B2, both of which are owned by the assignee of the present invention, the contents of which are hereby incorporated by reference. In operation, the stator assembly 56 is energized by an alternating signal provided by a circuit assembly 76. The alternating signal to the electromagnet will produce an electromagnetic interaction with permanent magnets 62, resulting in an oscillating motion of the oscillating arm 64 and movement of the contact member away from and then toward the application surface, e.g. the face, in particular the facial skin.

The applicator assembly includes a power switch 72 to initiate action of the motor and the contact member. The operation of motor 52 is controlled by a circuit assembly 76, which typically is a conventional microprocessor controller. There are three specific variables, among others, which can be controlled by circuit assembly 76 in the embodiment shown.

A first variable is the frequency of oscillation of the armature arm 64 and hence contact member 16. The movement of the contact member 16 is slightly arcuate, due to the configuration of the armature, but it is close to linear motion, toward and away from the skin of the user. The range of frequency is 50 Hz to 200 Hz, with a preferred range of 100 Hz to 140 Hz. Frequencies which are too low are less effective, while frequencies which are too high cause discomfort to the user. A second variable is the amplitude of movement of the contact member. The amplitude is within a range of 0.010 to 0.075 inches, with a preferred range of 0.020-0.035 inches. Amplitudes that are too low are less effective, while amplitudes which are too high cause discomfort to the user. A third variable is the time of operation of the device. This can be set for various times by the microprocessor but for example it is approximately 15 seconds for treating the skin around the eyes, for instance. It could be in the range of 5-40 seconds, depending on the condition being treated. Times that are too short are less effective, while times that are too long result in a decreased rate of absorption.

When the device is operating, i.e. when the contact member is moving back and forth, the user places the contact member lightly against the skin area where the formulation is to be applied. As one example, this could be in the vicinity of the eyes of the user, in order to reduce the wrinkles in that area of the facial skin. A number of other applications are possible, as explained in more detail below. The formulation, because of its viscosity, typically remains within the dish-shaped portion of the contact member. The formulation is absorbed at a high rate into the skin of the user by the tapping action produced by the applicator. A suitable range of formulation viscosity is 10,000 cps to 500,000 cps, while a preferred range is 50,000 cps to 200,000 cps. The action of the contact member against the skin results in a high-level effective absorption of the formulation into the skin, significantly more effective than by manual application or by any known non-manual applicators.

In operation, while the embodiment disclosed above includes an on/off switch, it should be understood that other means for initiating operation of the applicator can be used. This includes a proximity switch which would initiate operation upon initial contact with or close proximity of the contact member and the skin. Also, the length and configuration of the applicator disclosed above has been found to be advantageous for the particular motor disclosed, as it reduces significantly any vibration action of the motor being transferred to the handle. The applicator is hence easy and comfortable to use.

It should be understood that in operation, the article has a number of uses, for treatment of various skin conditions, depending upon the particular formulation used. For instance, anti-aging formulation products can be used. Since anti-wrinkle/anti-aging products all are quite expensive, the present embodiment, featuring a precise dispensing of a single dose of formulation into the contact member, is advantageous. Further, the contact member can be configured specifically to various specific single formulation doses, as discussed in more detail below. In other arrangements, moisturizers and other lotions can be used. Other common skin conditions can be treated besides crow's feet/wrinkles and aging spots, including skin enhancements, such as lip plumping.

Further, treatment for toenail fungus and athlete's foot can be accomplished with the article, with the proper formulations. The absorption of those formulations is enhanced, both in the skin area and on the nails, by use of the applicator. Still further, hair loss prevention and hair removal can be facilitated by using the appropriate formulations. Again, the applicator, using correct formulation dosages, can produce increased absorption of the treatment formulations, including those products which are specifically designed to treat topical hair loss as well as hair removal. A still further formulation can be used with the applicator to treat hyper/hypo pigmentation. Pigmentation of the skin typically occurs relatively deep within the epidermis, at the base membrane level. Treatment of the pigmented cells requires that any topical formulation must go deep within the skin. Instead of applying a treatment formulation two to three times a day for three months to achieve results, which is typical, the use of the present applicator can significantly decrease the time required for desirable results to be achieved, due to the deep absorption of the formulation made possible by the action of the applicator.

Still further, certain makeup, in particular lipstick and blush, can be effectively applied with the present applicator. In addition, temporary tattoos can be applied to the skin. In this application, a dye is moved by the action of the applicator into the deeper layers of the epidermis, but not the dermis, resulting in a non-permanent tattoo which lasts for an extended period of time, but will eventually fade, thereby eliminating the need for tattoo removal, which can be disfiguring, painful and expensive.

In addition, rapid teeth whitening can be accomplished with the applicator, using a gel-like whitening applied to the surface of the teeth.

Hence, the present invention has a large number of possible applications in which absorption is an important aspect of treatment. Various conditions can be effectively treated depending upon the formulation used.

In addition to the visible cosmetic benefits of the applicator, relaxation and massage benefits are possible. Use of the applicator around the sinus area, temples, behind the ears and at other pressure points can provide headache and stress relief.

FIGS. 6A and 6B-14A and 14B show top and cross-sectional views, respectively, of various possible contact member arrangements. FIGS. 6A and 6B show the cup-shaped configuration of a circular contact member discussed briefly above. FIGS. 7A and 7B show a circular embodiment 79 with a relatively shallow, flat inner surface 80 with a surrounding rounded lip 81, while FIGS. 8A and 8B show an embodiment with a circular groove 84 which is positioned between a rounded lip 86 of the contact member and a central flat surface 88. FIGS. 9A and 9B show a circular embodiment which is similar to FIGS. 6A and 6B except that the dish-shaped surface 89 extends to a knife edge 90, instead of a curved lip. FIGS. 10A and 10B show a circular contact member similar to FIGS. 7A and 7B, wherein the circular groove 92 and a center area 94 have straight boundary edges. FIGS. 11A and 11B show a circular contact member with a shallow center flat area 98 and a relatively narrow outer lip 100. FIGS. 12A and 12B and 13A and 13B show substantially square contact members, with contact member 102 in FIGS. 12A and 12B having a single groove 104 which is relatively shallow and close to outer edge 106 of the contact member, while contact member 110 in FIGS. 13A and 13B has a shallow flat central area 111, with a relatively narrow outer lip 112.

Contact member 114 shown in FIGS. 14A and 14B has a flat outer surface 116, used for tapping a formulation which is already present on the skin. The contact member can be made from an elastomeric material such as silicone rubber, soft enough to avoid discomfort or injury to the skin but firm enough to maintain its shape and impart sufficient sonic energy into the skin. Silicone rubber with hardness ranging between Shore 00-30 and Shore A-5 is preferred, but other materials can be used, such as natural rubber, butyl rubber and polyurethane.

As the above examples show, a variety of contact member arrangements and configurations can be used to carry out the function of the present invention.

Figure 15:
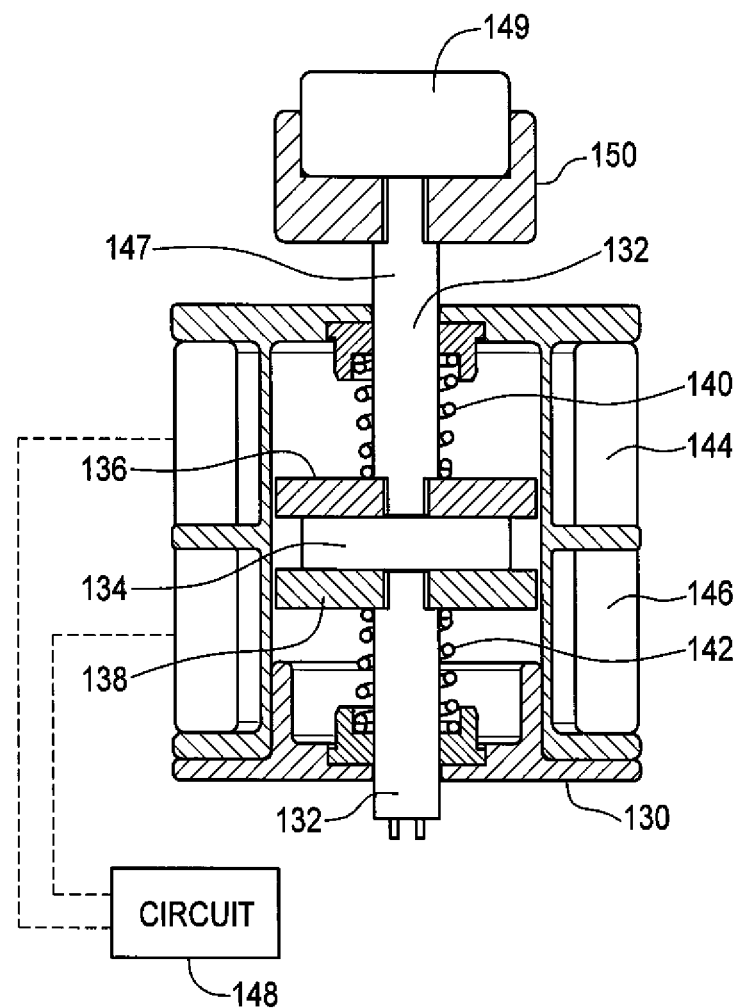
FIG. 15 is a cross-sectional view of another embodiment of the applicator.

FIG. 15 shows a portion of a different embodiment of the applicator assembly. In this embodiment, a housing 130 includes a central shaft 132 therein, a permanent magnet 134 mounted on the central shaft and two pole pieces 136, 138 positioned on opposite sides of the permanent magnet 134. Positioned between the pole pieces 136, 138, respectively, and the internal ends of the housing 130 are two coil springs 140, 142. Wound around the exterior of the housing are two spaced coils 144, 146. The coils 144, 146 in operation are energized with opposing alternating currents by an alternating current energizing circuit 148 so that as the coils are energized, the magnetic fields produced will interact with the permanent magnet 134, forcing shaft 132 in one direction over one half cycle for the alternating current signal, and then in the other direction over the other half cycle, thereby providing a linear back-and-forth movement of end 147 of the shaft 132, which extends outwardly from housing 130.

Mounted on the end 147 of shaft 132 is a contact member 149 which is mounted in a base member 150. The contact member 149 is conveniently replaceable by the user at appropriate intervals. Alternatively, the contact member may be permanently attached. The applicator produces a tapping action with the same ranges of frequency and amplitude discussed above. The configuration of the contact member can also vary, as discussed above. The embodiment of FIG. 15 can be used either with a reservoir assembly similar to that disclosed for the above embodiment, or can be used to improve absorption of the formulation already applied manually by a user.

Figure 16:
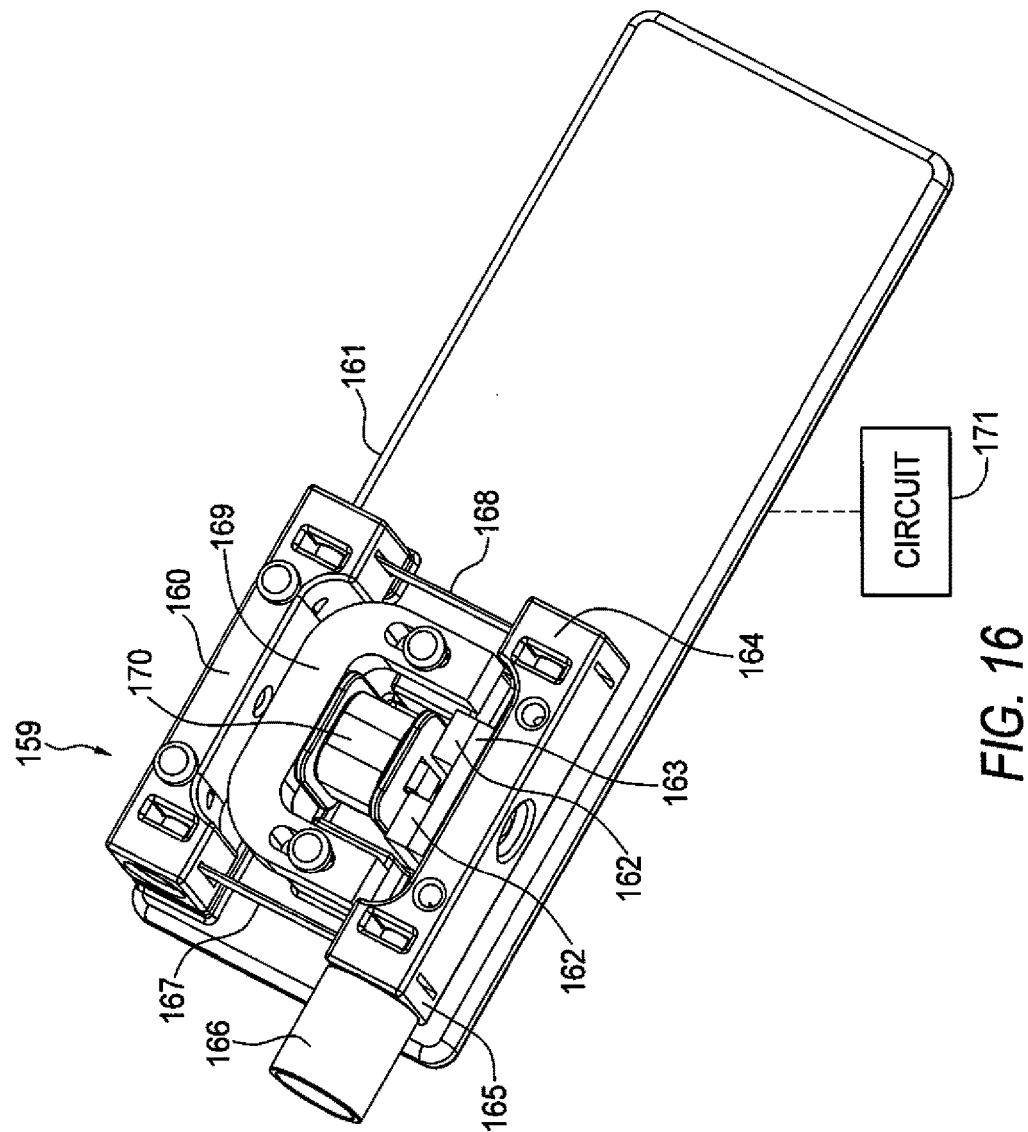
FIG. 16 is a perspective view of an applicator with an alternative motor arrangement.

FIG. 16 shows a portion of a different embodiment of the applicator assembly. In this embodiment, which shows a different motor 159, an anchor member 160 is mounted on a housing 161. Permanent magnets 162, 162 are mounted on a backiron 163 which in turn is mounted on an armature 164. Positioned at end 165 of armature 164 and mechanically mounted thereto is a contact member 166. The contact member 166 can be configured as described above, including having a concave end face. The contact member 166 extends outwardly from housing 161 and is replaceable by the user or may be permanently attached. Attached at both longitudinal ends of armature 164 and at both ends of anchor member 160 are cantilever springs 167, 168, i.e. springs 167, 168 each extend between the armature and the anchor member.

Wound around a center leg of stator assembly 169 is a coil 170. Coil 170 in operation is energized with opposing alternating current by an alternating current energizing circuit 171 so that as the coil is energized, the magnetic field produced will interact with the permanent magnets 162, 162, forcing armature 164 in one direction over one half cycle for the alternating current signal, and in the other direction over the other half cycle, thereby providing a linear back-and-forth movement, of contact member 166. The applicator 159 provides a tapping action with the same ranges of frequency and amplitude discussed above. The embodiment of FIG. 16 can be used either with a reservoir assembly similar to that disclosed for the above embodiment, or can be used to improve absorption of the formulation already applied manually by a user.

FIGS. 17-22 show another embodiment of the applicator which includes a cartridge with an integrated fluid path, referred to as a combined or integrated applicator. The integrated applicator is shown at 200 in FIG. 17. The combined applicator includes a motor assembly 202 and a cartridge assembly 204. The integrated applicator includes an on/off switch 206 and a contact member 208, which is part of a contact assembly 209, shown in more detail in FIG. 19, which in operation is moved reciprocally toward and away from the skin, in a manner similar to the above-described embodiments. The integrated applicator 200 also includes a fluid control button 110 which when operated results in fluid being expelled from a reservoir 212 through a connecting tube 214, then through a channel 216 in the contact assembly, and out through upper surface 218 of contact member 208.

As with the previous embodiments, upper surface 218 of contact member 208 can be concave or dish-shaped to hold a skin treatment formulation or similar fluid, as well as other configurations. The integrated applicator also includes a cap member 220 which can be snapped or slid on to cover the contact member. The cap member 220 can be applied to the cartridge assembly 204 when the cartridge assembly is attached to or separated from the motor assembly 202. The cartridge assembly 204 is removably secured to the motor assembly 202 by a latch mechanism 222. The cartridge assembly is coupled to the motor assembly by means of tabs 226-226 near the upper end of the cartridge assembly, which mate with corresponding slots 228-228 in the motor assembly, and by latch tab 222 which extends through slot 223 in the motor assembly, as well as magnetic elements on the two assemblies (not shown).

To secure the cartridge assembly to the motor assembly, the cartridge assembly is first moved horizontally to make contact with the motor assembly, and then moved downwardly relative to the motor assembly. This downward motion activates a spring-loaded cartridge release latch 230 which mates with the latch tab 222. To remove the cartridge, the release member 230 is simply moved to the right, which releases the latch tab 222, and then the cartridge is slid upwardly and then outwardly relative to the motor assembly.

Figure 19:
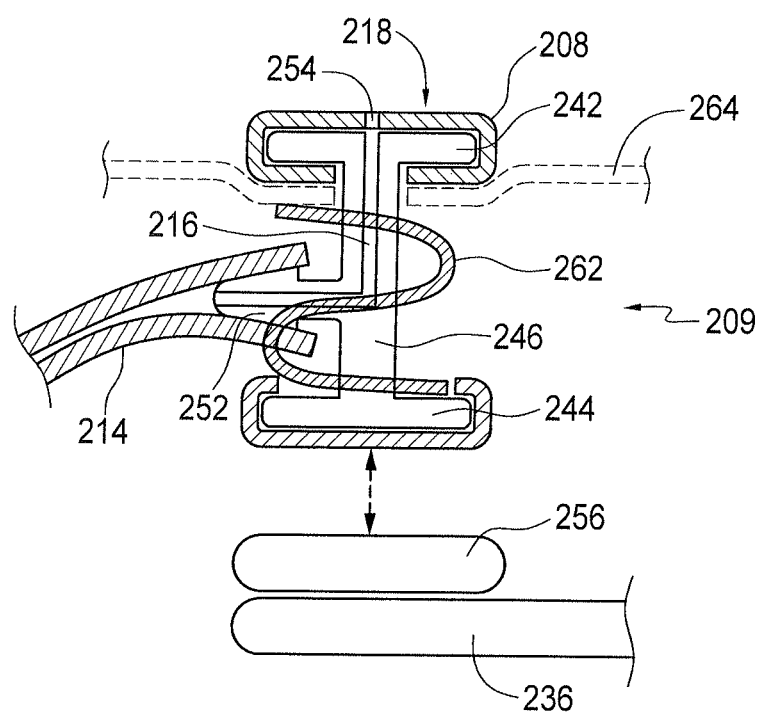
FIG. 19 is a cross-sectional view of a portion of FIG. 18A.

The motor assembly includes a motor 234 which can be of various arrangements, including those described above. It includes an output member 235 which, in operation, forces tang element 236 shown in FIG. 18B to move vertically, i.e. up and down, within the motor assembly. When the cartridge assembly and the motor assembly are engaged, tang 236 is positioned directly under a stem portion of the contact assembly. FIG. 19 shows a detailed view of this part of the applicator. The stem portion includes an upper portion 242, generally in the form of a disc, and a lower portion 244, also generally in the form of a disc. The upper and lower disc portions 242 and 244 are: connected by an integral intermediate portion 246. Partially surrounding the upper disc portion 242 is the contact member 208 which contacts the skin.

The intermediate portion 246 includes a fluid entry extension 252 which has channel 216 extending from a free end thereof through the intermediate portion and up to an opening 254 in the contact, member 208. Tube 214 from reservoir 212 is positioned around extension 252. There is thus a continuous fluid path between reservoir 212 and the upper surface of contact member 208. The lower portion 244 is surrounded by a magnetic cap, typically by swaging, the cap comprising, for example, a magnetic material such as magnetic stainless steel. When the cartridge assembly is inserted horizontally into the motor assembly, tang 236, which has a magnetic piece 256 at the free end thereof, typically consisting of a permanent magnet, is beneath but separate from the magnetic lower portion 244 of the stem portion of the contact assembly. When the cartridge assembly is then slid vertically downward, engaging the latch, the vertical motion results in the magnetic lower portion 244 contacting the magnetic piece 256. The magnetic attractive force supplied by the magnetic piece 256 is strong enough to maintain contact between the magnetic lower portion 244 and the magnetic piece 256 over the full range of motion of the tang 236, by action of the motor 234. The range of frequency and amplitude of the movement is the same as for the above embodiments.

Figure 17:
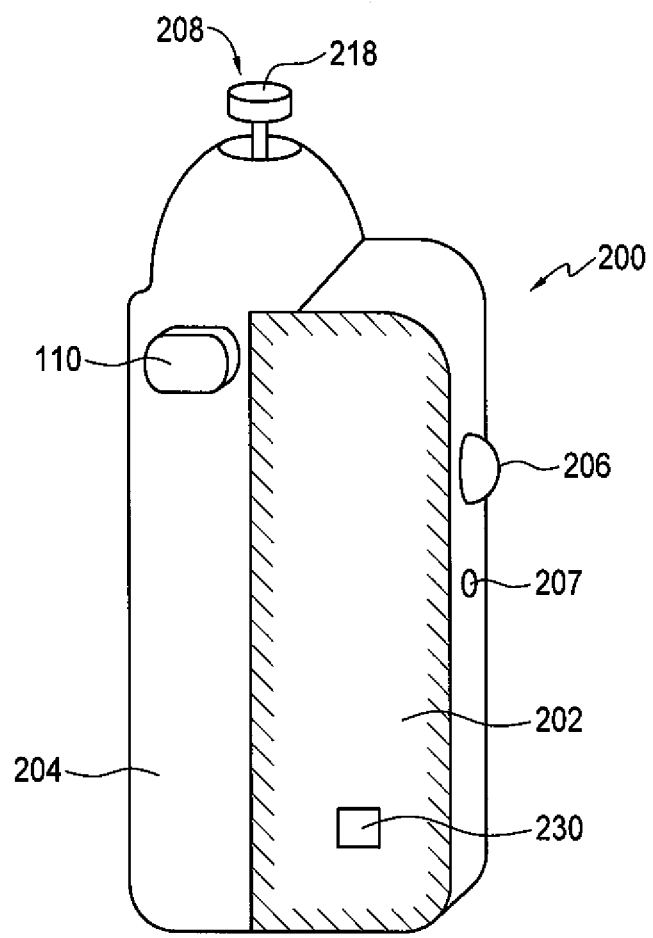
FIG. 17 is a perspective view of a cartridge/applicator embodiment.

Positioned around intermediate portion 246 is a spring 262 which is positioned against upper surface 264 of the cartridge assembly, so that it pushes downwardly on the lower portion 244, resulting in the lower surface of the upper portion 242 contacting or seating in circular recess 264 in the upper surface of the cartridge assembly when the cartridge assembly is separated from the motor assembly. When the cartridge assembly and the motor assembly are engaged, the upward force of tang 256 on magnetic portion 244 pushes the applicator upward against the force of the spring, resulting in the contact member 208 and upper portion 242 being pushed, upward and away from the upper surface 264 of the cartridge assembly. This extended position of the contact member and applicator is also shown in FIG. 17.

The operation of the motor results in an up and down motion of the tang, which is transmitted to the applicator and its contact member 208, and in turn against the skin.

Figure 20A:
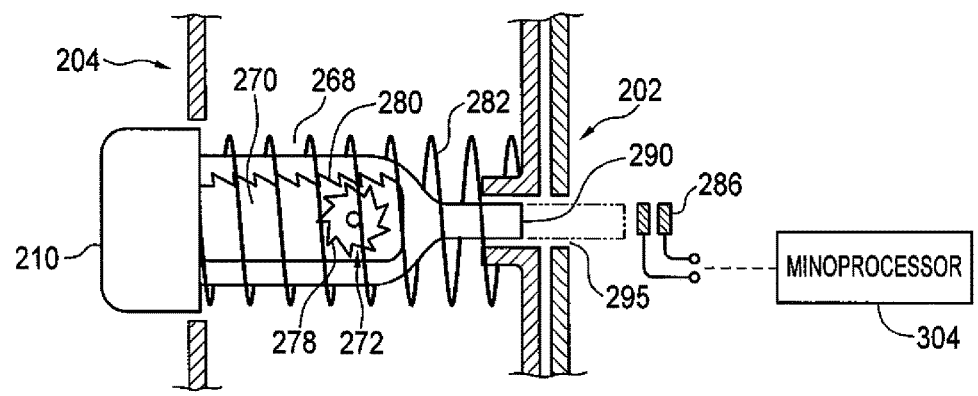
FIGS. 20A and 20B are cross-sectional views of the formulation-moving portion of FIG. 18A.
Figure 20B:
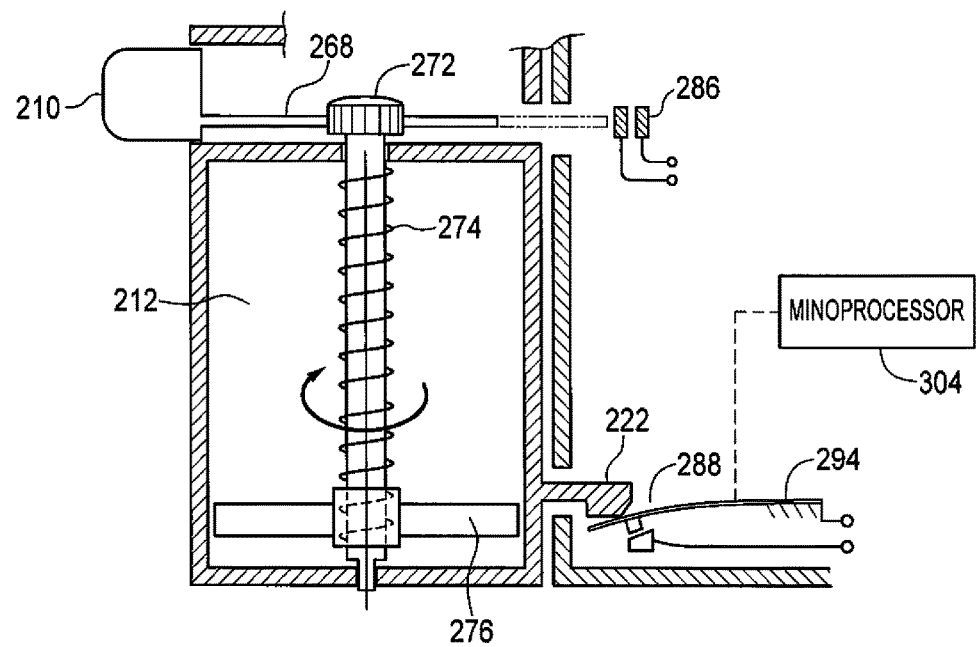

FIGS. 20A and 20B show cross sections of a portion of the cartridge assembly for moving the formulation in reservoir 212 up to the contact member 208. The fluid control button 210 shown in these figures is part of or connected to a rack member 268, which has an open center area 270. Positioned in the open center area is a pinion 272 which is connected to a threaded rod 274 which extends down into the reservoir 212. At the bottom of the threaded rod 274 is a plate 276. The pinion 272 has a serrated edge. 278 which engages interior teeth 280 on one border side of the open center area 270 of rack 268. Surrounding rack member 268 is: a spring 282.

In operation, when fluid control button 210 is pushed inwardly, rack member 268 turns pinion 272, which in turn rotates threaded rod 274, pulling plate 276 upwardly. This forces fluid out of the reservoir into tube 214 and from there to channel 216 into the contact member 208 (FIGS. 18, 19). Spring 282 tends to return button 210 back to its rest position, without turning the pinion, thereby maintaining plate 276 at its last position. Repeated operation of fluid control button 210 results in consistent, regular dispensing of the formulation onto the surface of contact member 208. This can be done while the motor/contact assembly is operating.

Still referring to FIGS. 20A and 20B, an interlock capability is provided by two microswitches 286 and 288 which prevent motor 234 from operating unless a cartridge assembly is installed and/or if a minimum amount of fluid has been expelled onto the contact member. Microswitch 286 is operated by end 290 of rack assembly 268, while microswitch 288 is operated by latch tab 222 which extends form cartridge assembly 204. End 290 extends through openings, 295 in the cartridge assembly and the motor assembly which are in registry while latch tab 222 extends through opening 292 in the motor assembly housing.

Microswitch. 288 is maintained in a non-operative, open position by spring 294. When tab 222 of the cartridge assembly comes into contact with microswitch 288, it overcomes the force of spring 294, such that microswitch 288 makes contact. End 290 of the rack assembly, extending through openings 295 in the cartridge assembly and the motor assembly, forces the microswitch 286 to make contact. Microswitches 286 and 288 are connected to a microprocessor 304 in the motor assembly 202. The microprocessor 304 examines the status of the microswitch closures 286 and 288. If the microprocessor senses that both microswitches are in a closed portion simultaneously, the microprocessor enables the motor drive. The user can actuate the control button 210 to move fluid into the contact member and enable the motor drive. The motor module can include an enable status indicator 207, such as a light emitting diode (LED), which the microprocessor illuminates when the drive motor is enabled, which informs the user that a sufficient volume of fluid has been dispensed for operation and that actuation of the article can be commenced. The user then can push the on/off button 206 to actuate the applicator action.

In the above arrangement, it is difficult to defeat the interlock system, for instance by inserting an object into the motor module to close the microswitch 206, since the logic in the microprocessor will detect that there is no cartridge present because microswitch 288 isn't simultaneously closed and prevent enabling the motor.

When the reservoir 212 is emptied, threaded rod 274 will have pulled plate 276 upwardly sufficiently that the pinion is prevented from moving, which prevents microswitch 286 from being activated. Before that point is reached, however, an indication that the reservoir will be shortly empty can be provided by the rod 274 being configured to have a somewhat larger diameter at its upper portion, so that when the reservoir is toward the end of its capacity, i.e. the last 50%, with a preferred range of 10-20%, the bottom plate is positioned on the larger diameter section and is hence harder to turn, providing feedback to the user that the cartridge is toward the end of its life. Also, wall of reservoir 212 can be made transparent, so that, the position of the bottom plate and the amount of fluid left in the reservoir can be easily determined.

Figure 21:
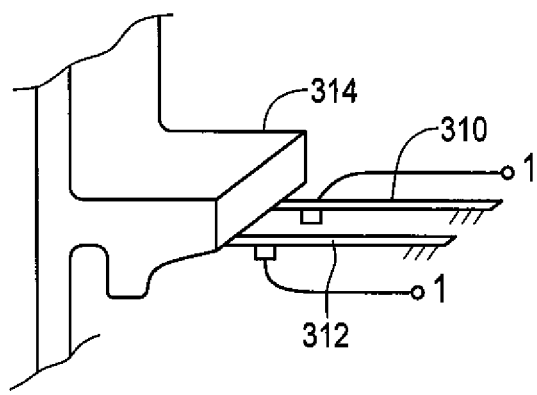
FIGS. 21 and 22 are perspective views of a cartridge-detection feature of FIG. 18A.
Figure 22:
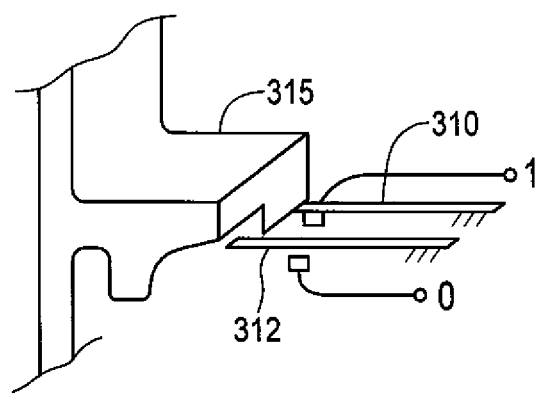

FIGS. 21 and 22 show an arrangement for distinguishing between cartridges which have different contact member configurations and/or different kinds of fluids, for different skin treatments. For instance, for wrinkle reduction treatment, using a formulation for that condition, the size of the contact member may be medium, with a relatively low power level and a specific operating time, e.g. 10 seconds. Another application, for lip plumping, may requite a larger contact member, a medium power level and a longer duration time, i.e. 20 seconds. For removal of age spots, the contact member would likely be small, with a higher power level and a duration time of 10 seconds. These are examples only. This operating information is stored in the microprocessor. The tab on the lower end of the cartridge assembly can be configured to identify the application through contact with the associated microswitch in the motor assembly. Two microswitches 310 and 312 can be used. The insertion of tab 314 in FIG. 21 will activate both microswitches, while the configuration of the tab 315 in FIG. 22 would activate only one microswitch. Two microswitches have the capability of identifying three different cartridges to the microprocessor, as well as the lack of a cartridge. Thus, the microprocessor can detect which type of cartridge has been installed and automatically implement operating parameters predetermined for that cartridge type.

The user can change cartridges by simply removing the particular one being currently used, by moving the latch release button and then sliding the old cartridge assembly up and off from the motor assembly. The entire fluid path, including the contact member, is removed with the cartridge assembly in this embodiment. The cap can be placed on the cartridge for protection and to prevent it from drying out. A different cartridge can then be used, which either may be the same type of cartridge for the same application or a different cartridge for a different application. Different cartridges, as indicated above, are used for different applications, including such applications as lines around the eyes, plumping the lips, age spots or other skin conditions or desired skin enhancements. In every case, however, removal of the cartridge removes the entire fluid path, including the applicator.

Prior to use of the applicator, the skin can be cleansed, such as by a sonic frequency skin cleansing device, such as shown in U.S. Pat. No. 7,320,691, which is owned by the assignee of the present invention, the contents of which are incorporated by reference.

Hence, an applicator and/or an integrated applicator has been disclosed which are capable of providing a relatively high speed, low amplitude mechanical action for use against the skin of a user, designed to increase, the absorption of skin formulations as well as other functions. Various skin formulations can be used in the treatment of various skin conditions. The applicator may include a formulation reservoir which in one embodiment is separable from an applicator which itself includes a contact member, while in another embodiment, the cartridge/reservoir assembly, including the fluid path and the contact assembly, is separable as an entire unit from the motor assembly. The device is adapted to provide either a single dose of the formulation into the contact member or other selected volumes of fluid upon actuation of a control button. In one embodiment, fluid can be dispersed to the contact member while the device is operation, in single dose amounts, or smaller.

Although a preferred embodiment of the invention has been disclosed here for the purposes of illustration, it should be understood that various changes, modifications and substitutions may be incorporated in the embodiment without departing from the spirit of the invention, which is defined by the claims which follow.

What is claimed is:

1. A formulation applicator for skin areas of the human body, comprising: a housing; a motor contained within the housing, the motor including a stator assembly and an armature assembly, the stator assembly including an electromagnet, the armature assembly including a moving member positioned in the vicinity of one end of the electromagnet having two spaced permanent magnets mounted thereon, wherein an armature arm extends from one end of the moving member, the armature arm in operation mechanically moving a mounting element which is directly connected thereto, wherein the armature arm and the mounting element move together positively, in an oscillating, bidirectional reciprocating manner by motor action to cyclically impact the skin area with a flexible contact member mounted on a forward end of the mounting element, toward to and away from the skin area, substantially perpendicular thereto, wherein the armature arm and the mounting element are without a rotating component in operation; and the flexible contact member with a non-sharpened edge mounted on the mounting element so that the contact member moves linearly to cyclically impact the skin area, the contact member moving with a frequency of 50 Hz to 200 Hz and an amplitude in the range of 0.010-0.075 inches, toward and away from the skin area, substantially perpendicular thereto, alternately against and then away from the skin area, acting to increase the absorption of skin formulations from a forward surface of the contact member into the skin area without pumping of the skin formulations and without removing skin material as the contact member impacts the skin area to which the formulation is being applied.

2. The applicator of claim 1, wherein the contact member is configured to hold a single dose or a single use of a selected formulation.

3. The applicator of claim 1, wherein the contact member is configured to hold less than or greater than a single dose or a single use of a selected formulation.

4. The applicator of claim 1, wherein the frequency range is between 110 Hz and 135 Hz, and the amplitude range is between 0.020 inches and 0.035 inches.

5. The applicator of claim 1, wherein the frequency range is between 110 Hz and 135 Hz.

6. The applicator of claim 1, wherein the amplitude range is between 0.020 inches and 0.035 inches.

7. The applicator of claim 1, wherein the applicator has an exterior configuration which can be conveniently held in the hand of a user.

8. The applicator of claim 7 wherein the applicator is otherwise configured so that motor action does not produce significant vibrations to the housing.

9. The applicator of claim 1, wherein the armature arm is connected to one end of a beam spring, the other end of which is mounted fixedly to a base member connected to the housing.

10. The applicator of claim 1, wherein the contact member extends outwardly from one end of the applicator.

11. The applicator of claim 10, including a circular groove located between a central area and a surrounding edge.

12. The applicator of claim 1, wherein the contact member is replaceable.

13. The applicator of claim 1, wherein the contact member is permanently attached.

14. The applicator of claim 1, wherein the contact member comprises an elastomeric member having a Durometer value between Shore 00-30 to Shore A-5.

15. The applicator of claim 14, wherein the contact member is silicone gel.

16. The applicator of claim 1, wherein the contact member has a circular exterior configuration and a cupped central area in a contact surface for receiving the formulation.

17. The applicator of claim 1, wherein the contact member is circular in outline and includes a contact surface having a circular groove therein for receiving the formulation.

18. The applicator of claim 1, wherein the contact element has a substantially square outline and a contact surface central area which is lower than a surrounding edge for receiving the formulation.

19. The applicator of claim 1, wherein the contact element has a substantially square outline and a groove in a contact surface for receiving the formulation.

20. The applicator of claim 1, wherein the contact member has a contact surface which is flat.

21. The applicator of claim 1, including a formulation reservoir assembly which is positionable at one end of the applicator assembly, wherein the reservoir assembly includes an exit member which is configured to dispense formulation onto the contact element when the reservoir assembly is positioned on the applicator assembly, or when the reservoir is separated from the applicator assembly.

22. The applicator of claim 21, wherein the reservoir assembly includes a pusher plate therein and a control assembly which includes an element for moving the pusher plate within the reservoir and a member which is operable by a user to adjust the pusher plate within the reservoir to load a formulation amount through the exit member into the contact member.

23. The applicator of claim 1, wherein the formulation is a skin treatment formulation.

24. A formulation applicator for skin areas of the human body, comprising:

a housing;

a motor contained within the housing, the motor including a stator assembly and an armature assembly, the stator assembly including an electromagnet, the armature assembly including a moving member positioned in the vicinity of one end of the electromagnet having two spaced permanent magnets mounted thereon, wherein an armature arm extends from one end of the moving member, the armature arm in operation mechanically moving a mounting element which is directly connected thereto, wherein the armature arm and the mounting element move together positively, in an oscillating, bidirectional reciprocating manner by motor action to cyclically impact the skin area with a flexible contact member mounted on a forward end of the mounting element, toward and away from the skin area, substantially perpendicular thereto, wherein the armature arm and the mounting element are without a rotating component in operation; and the contact member with a non-sharpened edge mounted on the mounting element so that the contact member moves linearly to repeatedly impact the skin area, the contact member comprising a flexible material which is soft enough to avoid discomfort or injury to the skin but firm enough to impart sufficient sonic energy into the skin, the contact member moving with a frequency of 50 Hz to 200 Hz and an amplitude in the range of 0.010-0.075 inches, toward and away from the skin area, substantially perpendicular thereto, alternately against and then away from the skin area, acting to increase the absorption of skin formulation into the skin area without removing skin material as the contact member impacts the skin area to which the formulation is being applied.

* * * * *